United States Patent [19]
Maeda et al.

[11] Patent Number: 5,952,512
[45] Date of Patent: Sep. 14, 1999

[54] PRODUCTION OF OPTICALLY ACTIVE BENZOTHIEPIN SALTS

[75] Inventors: Yoshiharu Maeda, Tondabayashi; Motoki Ikeuchi, Nishinomiya; Shigeo Yabuno, Osaka, all of Japan

[73] Assignee: Takeda Chemical Industries, Ltd., Osaka, Japan

[21] Appl. No.: 08/702,675

[22] PCT Filed: Jul. 23, 1996

[86] PCT No.: PCT/JP96/02056

§ 371 Date: Sep. 11, 1996

§ 102(e) Date: Sep. 11, 1996

[87] PCT Pub. No.: WO97/03989

PCT Pub. Date: Feb. 6, 1997

[30] Foreign Application Priority Data

Jul. 24, 1995 [JP] Japan .................................. 7-187450

[51] Int. Cl.⁶ .................................................. C07D 337/12
[52] U.S. Cl. .................................................................. 549/12
[58] Field of Search ................................................. 549/12

[56] References Cited

U.S. PATENT DOCUMENTS

| | | | |
|---|---|---|---|
| 3,966,752 | 6/1976 | Asinger et al. | 548/147 |
| 5,158,943 | 10/1992 | Sohda et al. | 514/96 |
| 5,726,325 | 3/1998 | Yoshida et al. | 549/48 |

FOREIGN PATENT DOCUMENTS

| | | |
|---|---|---|
| 0128684 | 12/1984 | European Pat. Off. . |
| 0376197 | 7/1990 | European Pat. Off. . |
| 0460488 | 12/1991 | European Pat. Off. . |
| 0719782 | 7/1996 | European Pat. Off. . |
| 60-224672 | 9/1985 | Japan . |

OTHER PUBLICATIONS

The Merck Index (1996), pp. 817 and 5667.
Liebigs Ann. Chem. (1982) 1995–1998.
Soda et al, "Preparation of Sulfur–containing heterocyclic compounds for the treatment of osteoporosis", Chem.Abs. 121:83085, 1993.
Sohda et al, "Preparation of 1,2,4,5–tetrahydro–5–oxobenzothiepines for prevention of treatment of osteoporosis", Chem. Abs. 116:151599, 1991.

*Primary Examiner*—Deborah C. Lambkin
*Attorney, Agent, or Firm*—Fitzpatrick, Cella, Harper & Scinto

[57] ABSTRACT

A method of producing an amine salt of an optically active benzothiepin derivative, which is characterized by allowing a benzothiepin derivative represented by the formula (I)

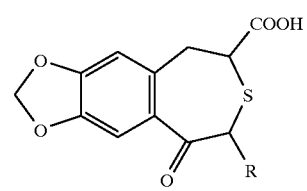

wherein R stands for a lower alkyl group, to react with an optically active amine.

8 Claims, No Drawings

PRODUCTION OF OPTICALLY ACTIVE BENZOTHIEPIN SALTS

DESCRIPTION

This application is a 371 of PCT/JP96/02056 filed Jul. 23, 1996.

TECHNICAL FIELD

This invention relates to an amine salt of an optically active benzothiepin derivative useful as a raw material of a pharmaceutical agent having an activity of accelerating bone formation and an activity of suppressing bone resorption, and to a method of producing it.

BACKGROUND ART

The present applicants found an optically active compound useful as a pharmaceutical agent having an activity of bone formation and a bone resorption activity, i.e. a prophylactic and therapeutic agent of bone diseases, and have filed a patent application on this compound [EP-A-719782, Application Number 95 120444.5].

As methods of optically resolving a racemic modification, a mixture of optically active compounds, there have been generally employed, on a laboratory scale, and, in very limited cases, on an industrial scale, (1) preferential crystallization from a racemic modification, (2) a diastereomer method using an agent of optical resolution, (3) a fractionating method using a column chromatography packed with an optically active substance, (4) a fractionating method utilizing the stereospecificity of enzymatic reaction and (5) a fractionating method using an optically active film.

As examples of norephedrine subjected to optical resolution of optical isomers, descriptions are found in, for example, JPA S60(1985)-224672, JPA S48(1973)-23724 (U.S. Pat. No. 3,966,752), Liebigs Ann. Chem. p.1995 (1982) and EP-A-128684. However, these are nothing more than examples attempted for a certain specific compound. In other words, since no general regularity has been established on the optical resolution of optical isomers, when conducting optical resolution of optical isomers, various methods have to be investigated on respective compounds at the present technical level in the relevant field.

So far, production of an optically active benzothiepin derivative which is a raw material of the above-mentioned optically active compound useful as a prophylactic and therapeutic agent of bone diseases, especially an optically active 3-benzothiepin-2-carboxylic acid derivative, has been conducted by, for example, allowing a racemic isomer of 1,2,4,5-tetrahydro-4-methyl-7,8-methylenedioxy-5-oxo-3-benzothiepin-2-carboxylic acid to react with methyl mandelate, followed by recrystallization utilizing the difference in solubilities of diastereomers of the resulting ester derivative. This method, however, requires the formation of ester linkage and re-cleavage, and produces a relatively large amount of undesirable by-products, which requires complicated refining steps resulting in a low yield, thus a number of problems have been left to be solved for realizing the production on an industrial scale.

Circumstances being such as above, development of a method of producing efficiently an optically active benzothiepin derivative, especially (2R,4S)-1,2,4,5-tetrahydro-4-methyl-7,8-methylenedioxy-5-oxo-3-benzothiepin-2-carboxylic acid, as an optically active form in a substantially pure state, has been desired.

And, since the above-mentioned optically active compound useful as a prophylactic and therapeutic agent of bone diseases varies in its pharmaceutical activity and absorbability (especially oral absorbability), depending on the kind of an optically active form, production of a specific optically active compound which is excellent in a pharmaceutical activity and absorbability is desired. Accordingly, development of a method of producing an optically active benzothiepin derivative which is a raw material for production of the specific optically active compound is desired.

DISCLOSURE OF INVENTION

Taking the above circumstances into consideration, the present inventors have diligently conducted research work to find out an industrially advantageous method of producing an optically active benzothiepin derivative in a high purity and with a high yield by a simple procedure. As a result, they found out, unexpectedly, that a highly pure optically active benzothiepin derivative can be readily produced in a high yield by allowing a racemic mixture, trans-1,2,4,5-tetrahydro-4-methyl-7,8-methylenedioxy-5-oxo-3-benzothiepin-2-carboxylic acid, to react with an optically active amine to form a novel optically active amine salt, followed by separation thereof, thus the present invention has been accomplished.

More specifically, the present invention relates to (1) a method of producing an amine salt of an optically active benzothiepin derivative, which is characterized by allowing a benzothiepin derivative represented by the formula (I)

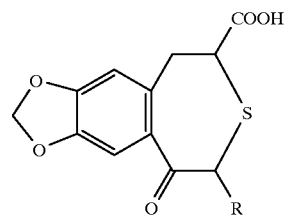

wherein R stands for a lower alkyl group, to react with an optically active amine;

(2) the method according to (1), in which the optically active amine is an optically active phenyl amino alkanol;

(3) the method according to (2), in which the optically active phenyl amino alkanol is an optically active form of a compound represented by the formula (II)

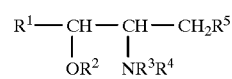

wherein $R^1$ stands for an optionally substituted phenyl group; $R^2$, $R^3$ and $R^4$ independently stand for H or a lower alkyl group; and $R^5$ stands for H, hydroxyl group, a lower alkyl group or a lower alkoxy group, or a salt thereof;

(4) a method of producing an optically active benzothiepin derivative, which is characterized by subjecting the amine salt of an optically active benzothiepin derivative described in (1) above to deamination; and (5) an optically active form of a compound represented by the formula (III)

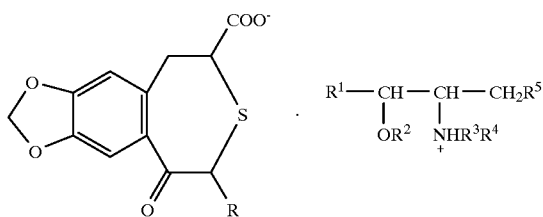

wherein R stands for a lower alkyl group; $R^1$ stands for an optionally substituted phenyl group; $R^2$, $R^3$ and $R^4$ independently stand for H or a lower alkyl group; and $R^5$ stands for H, hydroxyl group, a lower alkyl group or a lower alkoxy group.

Explanations of various definitions included in the above general formulae and the scope of this invention and preferable examples thereof are set forth below.

In the above-mentioned formulae (I) and (III), the "lower alkyl group" shown by R is exemplified by a $C_{1-6}$ straight chain or branched alkyl group such as methyl, ethyl, propyl, isopropyl, butyl, isobutyl, sec-butyl, tert-butyl, pentyl, isopentyl, neopentyl and hexyl, preferably a $C_{1-4}$ alkyl group such as methyl and ethyl. Among them, methyl is especially preferable.

In the compound represented by the formula (I) (hereinafter referred to as compound (I)), there exist R and S optical isomers respectively relative to asymmetric carbon atoms at 2- and 4-position of the 3-benzothiepin ring, namely, four types of optical isomers, i.e. (2R,4R)-coordinated, (2S,4S)-coordinated, (2S,4R)-coordinated and (2R,4S)-coordinated ones. While a mixture of these four isomers (a racemic mixture) can be employed, especially the trans-coordinated optical isomers, i.e. a mixture of two types of optical isomers (a racemic mixture), i.e. (2S,4R)-coordinated and (2R,4S)-coordinated ones, are preferable.

Practical examples of the compound (I) include (2R,4S)-1,2,4,5-tetrahydro-4-methyl-7,8-methylenedioxy-5-oxo-3-benzothiepin-2-carboxylic acid and (2S,4R)-1,2,4,5-tetrahydro-4-methyl-7,8-methylenedioxy-5-oxo-3-benzothiepin-2-carboxylic acid, with preference given to a mixture thereof (a racemic mixture).

In the above formulae (II) and (III), the phenyl group of "optionally substituted phenyl group" shown by $R^1$ may optionally have 1 to 2 optional substituents at any possible position. Examples of the substituents include optionally substituted alkoxy groups (e.g. $C_{1-3}$ alkoxy such as methoxy, ethoxy and propoxy), halogen atoms (e.g. fluorine, chlorine, bromine and iodine) and optionally substituted alkyl groups (e.g. $C_{1-3}$ alkyl such as methyl, ethyl and propyl). The alkoxy groups and alkyl groups may optionally have 1 to 2 optional substituents at any possible position. Examples of the substituents include phosphono group and mono- or di-$C_{1-3}$ alkoxyphosphoryl group (e.g. dimethoxyphosphoryl and diethoxyphosphoryl). As $R^1$, phenyl is mentioned as an especially preferable one.

In the above formulae (II) and (III), $R^2$, $R^3$ and $R^4$ independently stand for H or a lower alkyl group. Examples of the "lower alkyl group" include, like the afore-mentioned "lower alkyl group" shown by R, $C_{1-6}$ straight chain or branched alkyl groups, preferably $C_{1-4}$ straight chain or branched alkyl groups such as methyl and ethyl, especially preferably methyl. As $R^2$, H is more preferable. When $R^2$ is H, $R^3$ or $R^4$ is preferably H. Especially, it is more preferable that all of $R^2$, $R^3$ and $R^4$ are H.

In the above-mentioned formulae (II) and (III), $R^5$ stands for H, hydroxyl group, a lower alkyl group or a lower alkoxy group. As the "lower alkyl group", mention is made of, like in the case of above-described "lower alkyl group" shown by R, $C_{1-6}$ straight chain or branched alkyl groups, preferably $C_{1-4}$ straight chain or branched alkyl groups such as methyl and ethyl, especially preferably methyl. As the "lower alkoxy group", mention is made of $C_{1-3}$ alkoxy such as methoxy, ethoxy and propoxy, especially preferably methoxy. More preferable examples of $R^5$ include H and hydroxyl group.

As an optically active amine, mention is made of an optically active phenylamino alkanol.

Practical examples of the optically active phenylamino alkanol include an optically active form of a compound represented by the above-mentioned formula (II) (hereinafter referred to as compound (II)) or a salt thereof.

As salts of the compound (II), mention is made of salts with an inorganic base, salts with an organic base, salts with an inorganic acid, salts with an organic acid and salts with a basic or acidic amino acid.

Preferable examples of salts with an inorganic base include alkali metal salts such as sodium salts and potassium salts; alkaline earth metal salts such as calcium salts and magnesium salts; and aluminum salts, ammonium salts or the like. Preferable examples of salts with an organic base include those with, for example, trimethylamine, triethylamine, pyridine, picoline, ethanolamine, diethanolamine, triethanolamine, dicyclohexylamine and N,N'-dibenzylethylenediamine. Preferable examples of salts with an inorganic acid include those with, for example, hydrochloric acid, hydrobromic acid, nitric acid, sulfuric acid or phosphoric acid. Preferable examples of salts with an organic acid include those with, for example, formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. Preferable examples of salts with a basic amino acid include those with, for example, arginine, lysine or ornithine, and, preferable examples of salts with an acidic amino acid include those with, for example, aspartic acid or glutamic acid. Salts of the compound (II) are preferably salts with an inorganic acid, especially preferably salts with hydrochloric acid or sulfuric acid.

The compound (II) may be used in the form of salts and the compound (II) is preferably used in a free form.

Practical examples of the compound (II) include norephedrine such as (1R,2S)-norephedrine and (1S,2R)-norephedrine, or (1S,2S)-2-amino-1-phenyl-1,3-propanediol, with preference given to norephedrine. For the purpose of obtaining selectively an optically active form of (2R,4S)-coordinated compound (I), the compound (II) is more preferably (1R,2S)-norephedrine.

The reaction of the compound (I) with an optically active amine is conducted by mixing the compound (I) with the optically active amine, preferably in an organic solvent, followed by crystallization or recrystallization. The optically active amine can be used in an optional ratio relative to the compound (I), specifically in about 0.3 to 2 equivalent amount and preferably in about 0.5 to 1 equivalent amount relative to the compound (I). The reaction temperature ranges from −20° C. to the boiling point of the solvent employed, preferably from 0° C. (ice-cooling) to the boiling point of the solvent employed, more preferably around room temperatures (0° C. to 30° C.). The reaction time ranges from immediately after crystallization to 100 hours, preferably from 0.5 to 50 hours, more preferably 1 to 10 hours.

As the organic solvent, any organic solvent can be employed so long as it dissolves the compound (I) and does not interfere with the reaction.

Examples of the organic solvent include aromatic hydrocarbons such as benzene, toluene, and xylene; ethers such as dioxane, tetrahydrofuran (THF) and dimethoxyethane; alcohols such methanol, ethanol and propanol; esters such as ethyl acetate; nitriles such as acetonitrile; amides such as N,N-dimethylformamide; sulfoxides such as dimethylsulfoxide; halogenated hydrocarbons such as chloroform, dichloromethane, 1,2-dichloroethane, 1,1,2,2-tetrachloroethane; ketones such as acetone and 2-butanone. These organic solvents may be used as a mixture thereof in a suitable ratio or as a mixture with water. While it is preferable to suitably decide the volume of the organic solvent to be employed depending on individual reactions, the volume ranges, in general, from 5 to 100 times as much weight of the compound (I).

For the purpose of conducting optical resolution efficiently, optionally used are inorganic bases such as sodium hydroxide, potassium hydroxide, potassium carbonate, sodium carbonate, sodium hydrogencarbonate; or organic salts exemplified by tertially amines such as pyridine, triethylamine and N,N-dimethylaniline. The used amount of these bases is, for example 0.1 to 5 equivalents, preferably 0.5 to 2 equivalents, relative to the compound (I).

A process of crystallization or recrystallization is carried out by using a suitable solvent in accordance with a per se known method. As the solvent, mention is made of substantially the same solvent as the above-mentioned organic solvents, with preference given to ethers and alcohols, with further preference given to methanol and tetrahydrofuran. While it is preferable to suitably decide the temperature in the process of crystallization or recrystallization depending on individual reactions, the temperature practically ranges from −20° C. to the boiling point of the solvent employed, preferably from 0° C. (ice-cooling) to the boiling point of the solvent employed, more preferably around room temperatures (0° C. to 30° C.). In the above-mentioned reaction, from the viewpoint of efficiency of the processes, the organic solvent used in the reaction is preferably the same one as used in the process of crystallization or recrystallization. The amine salt of the optically active benzothiepin derivative may, depending on necessity, optionally be further refined by crystallization or recrystallization in accordance with known procedures.

By the method of this invention, an amine salt of an optically active benzothiepin derivative can be obtained as an optically active form in a substantially pure state. The said amine salt can be further purified optically by application of a known optical resolution method of a racemic mixture.

The amine salt of an optically active benzothiepin derivative obtained by the method of the present invention can be converted to the desired optically active benzothiepin derivative by subjecting the former to deamination. The deamination process is conducted in accordance with a known process. As the deamination process, mention is made of (i) a process comprising the reaction with an acid (e.g. HCl, $H_2SO_4$ and $HNO_3$) and (ii) a process comprising the reaction with an alkali (NaOH, KOH, $K_2CO_3$ and $NaHCO_3$), especially (i) is preferable.

The optically active benzothiepin derivative thus obtained can be used as a raw material of a pharmaceutical agent useful as a prophylactic and therapeutic agent of bone diseases which is disclosed in EP-A-719782.

Hereinafter described in detail are 1) the present method of producing an optically active benzothiepin derivative, and 2) a method of producing an optically active compound useful as a prophylactic and therapeutic agent of bone diseases by applying the optically active benzothiepin derivative.

In the case where, as the compound (I), for example, a mixture of (2R,4S)-1,2,4,5-tetrahydro-4-methyl-7,8-methylenedioxy-5-oxo-3-benzothiepin-2-carboxylic acid and (2S,4R)-1,2,4,5-tetrahydro-4-methyl-7,8-methylenedioxy-5-oxo-3-benzothiepin-2-carboxylic acid is employed, either one of (2R,4S)-1,2,4,5-tetrahydro-4-methyl-7,8-methylenedioxy-5-oxo-3-benzothiepin-2-carboxylic acid or (2S,4R)-1,2,4,5-tetrahydro-4-methyl-7,8-methylenedioxy-5-oxo-3-benzothiepin-2-carboxylic acid can be obtained as a highly pure optically active form which contains no substantial amount of the other one in accordance with the method of this invention. Subsequently, these optically active forms can be converted, by the method described in EP-A-719782, to respectively (2R,4S)-N-[4-(diethoxyphosphorylmethyl)phenyl]-1,2,4,5-tetrahydro-4-methyl-7,8-methylenedioxy-5-oxo-3-benzothiepin-2-carboxamide and (2S,4R)-N-[4-(diethoxyphosphorylmethyl)phenyl]-1,2,4,5-tetrahydro-4-methyl-7,8-methylenedioxy-5-oxo-3-benzothiepin-2-carboxamide, which are optically active compounds useful as prophylactic and therapeutic agents of bone diseases.

These optically active compounds are produced by reacting the above-mentioned optically active form or its reactive derivative at the carboxyl group or salt, with a compound represented by the formula (IV)

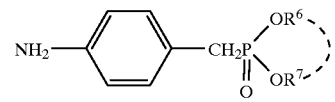

wherein $R^6$ and $R^7$ independently stand for a lower alkyl group, or a lower alkylene group by combination thereof, or its reactive derivative at the amino group or salt.

As the "lower alkyl group" shown by $R^6$ and $R^7$, mention is made of $C_{1-6}$ straight-chain or branched alkyl groups like the afore-mentioned "lower alkyl group" shown by R. When $R^6$ and $R^7$ are combined with each other to form a lower alkylene group,

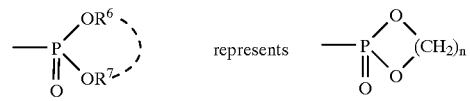

wherein n is an integer from 2 to 4. $R^6$ and $R^7$ are preferably $C_{1-4}$ alkyl groups such as methyl and ethyl.

Preferable reactive derivatives of the optically active form at the carboxyl group include acid halides, acid anhydrides, activated amides and activated esters, all obtained by conventional methods. More specifically, such preferable reactive derivatives include acid chlorides; acid azides; mixed acid anhydrides such as those with a substituted phosphoric acid such as dialkylphosphoric acid, phenylphosphoric acid, diphenylphosphoric acid, dibenzylphosphoric acid and halogenated phosphoric acid, or with dialkylphosphorous acid, sulfurous acid, thiosulfuric acid or sulfuric acid, or with a sulfonic acid such as methanesulfonic acid, or with an aliphatic carboxylic acid such as acetic acid, propionic acid, butyric acid, isobutyric acid, pivalic acid, pentanoic acid, isopentanoic acid or trichloroacetic acid, or with an aromatic carboxylic acid such as benzoic acid; symmetric acid anhydrides; activated amides with imidazole, 4-substituted imidazole, dimethylpyrazole, triazole or tetrazole; activated esters such as cyanomethyl ester, methoxymethyl ester, dimethyliminomethyl ester, vinyl ester, propargyl ester, p-nitrophenyl ester, tri-chlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester and 8-quinolylthio ester; and esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole and N-hydroxy-5-norbornane-2,3-dicarboximide. These reactive derivatives can be optionally chosen according to the type of the optically active form used.

Preferable reactive derivatives of the compound (IV) at the amino group include Schiff's base type imino or enamine form tautomeric isomers resulting from reaction of the compound (IV) with a carbonyl compound such as aldehyde (e.g., acetaldehyde) or ketone (e.g., acetone); silyl derivatives resulting from reaction of the compound (IV) with a silyl compound such as bis(trimethylsilyl)acetamide, mono (trimethylsilyl)acetamide or bis(trimethylsilyl)urea; and derivatives resulting from reaction of the compound (IV) with phosphorus trichloride or phosgene.

Preferable salts of reactive derivatives of the optically active form or the compound (IV) include salts with bases, exemplified by alkali metal salts such as sodium salt and potassium salt; alkaline earth metal salts such as calcium salt and magnesium salt; ammonium salt; and organic base salts such as trimethylamine salt, triethylamine salt, pyridine salt, picoline salt, dicyclohexylamine salt and N,N-dibenzylethylenediamine salt.

This reaction is normally carried out in a commonly used solvent such as water, an alcohol such as methanol or ethanol, acetone, dioxane, acetonitrile, chloroform, dichloromethane, 1,2-dichloroethane, tetrahydrofuran, ethyl acetate, N,N-dimethylformamide or pyridine, but can be carried out in any other organic solvent, as long as it does not interfere with the reaction. These ordinary solvents may be used in mixture with water.

When the optically active form or the compound (IV) is used in the form of free acid or salt thereof, this reaction is preferably carried out in the presence of an ordinary condensing agent, e.g., N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide or its hydrochloride; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; diphenylphosphorylazide; thionyl chloride; oxalyl chloride; a lower alkyl haloformate such as ethyl chloroformate and isopropyl chloroformate; triphenylphosphine; 2-ethyl-7-hydroxybenzisoxazolium salt, 2-ethyl-5-(m-sulfophenyl) isoxazolium hydroxide intramolecular salt; N-hydroxybenzotriazole; 1-(p-chlorobenzenesulfonyloxy)-6-chloro-1H-benzotriazole; or in what is called Vilsmeier's reagent as prepared by reaction of N,N'-dimethylformamide with thionyl chloride, phosgene, trichloromethyl chloroformate, phosphorus oxychloride, or the like. It is also preferable to use a condensing agent such as N,N'-dicyclohexylcarbodiimide in the presence of N-hydroxybenzotriazole or N-hydroxy-5-norbornan-endo-2,3-dicarboximide.

This reaction may also be carried out in the presence of an inorganic or organic base such as alkali metal hydrogen carbonate, tri(lower)alkylamine, pyridine, N-(lower) alkylmorpholine or N,N-di(lower)alkylbenzylamine. Although the reaction temperature is not subject to limitation, this reaction is normally carried out under cooling to heating (−10 to 120° C.) conditions. Reaction time is normally about 0.5 to 100 hours, preferably about 1 to 50 hours.

An optically active compound thus obtained may be isolated and purified by known means of separation and purification such as concentration, concentration under reduced pressure, solvent extraction, crystallization, recrystallization, redissolution and chromatography.

Thus, a specific optically active compound which is excellent in a pharmaceutical activity and absorbability can be produced.

An optically active form of the compound represented by the formula (III) (hereinafter referred to as compound (III)) is produced by reacting the compound (I) with an optically active form of the compound (II) or a salt thereof. This reaction is carried out in accordance with the above-mentioned reaction of the compound (I) with the optically active amine.

The optically active form of the compound (III) thus obtained is remarkably advantageous intermediate for synthesizing an optically active benzothiepin derivative in a substantially pure state.

The optically active form of the compound (III) is especially preferably (2R,4S)-1,2,4,5-tetrahydro-4-methyl-7,8-methylenedioxy-5-oxo-3-benzothiepin-2-carboxylic acid-(1R,2S)-norephedrine salt.

The following working examples and reference examples will explain the present invention in more detail, but these are mere examples and by no means intended to limit the scope of this invention. These examples may be modified to an extent not deviating from the scope of this invention.

NMR spectra were measured by means of Bruker DPX-300 spectrometer using, as the internal or external standard, tetramethylsilane, and all the delta values were expressed by ppm. The percent (%) used referring to a solution means gram numbers in 100 ml of the solution.

Optical purity of an optically active form was represented in terms of area percentages which were determined by subjecting 20 $\mu$L of a solution wherein 2 mg of an amine salt of an optically active benzothiepin derivative is dissolved in 20 mL of a mobile phase to a high performance liquid chromatography using a reversed phase column.
(conditions of high performance liquid chromatography)
Column; ULTRON ES-CD (Shinwa Kako KK) 150×6.0 mmI.D. Mobile phase; 0.02M $KH_2PO_4$(pH 3.0) :methanol:acetonitrile=9:1:1 (v/v/v)
Elution rate; 1.4 mL/min
Detection; UV236 nm The respective symbols in working examples have the following meanings.

s: singlet
d: doublet
t: triplet
q: quartet
dd: double doublet
br s: broad singlet
J: coupling constant
Hz: Herz

WORKING EXAMPLE 1

Production of (2R,4S)-1,2,4,5-tetrahydro-4-methyl-7,8-methylenedioxy-5-oxo-3-benzothiepin-2-carboxylic Acid. (1R,2S)-norephedrine Salt In 5 mL of methanol was suspended 0.5 g of a racemic mixture, 1,2,4,5-tetrahydro-4-methyl-7,8-methylenedioxy-5-oxo-3-benzothiepin-2-carboxylic acid (content 99.5%; trans compound 88.1%, cis compound 11.4%). To the suspension was added 0.27 g (1 equivalent) of (1R,2S)-norephedrine, which was once made into a solution, followed by crystallization in about 5 minutes. Then, the crystals were aged for 30 minutes at room temperature (25° C.). The crystals were collected by filtration, washed with 5 mL of cold methanol and dried overnight at room temperature under reduced pressure to afford 0.25 g of substantially pure (2R,4S)-1,2,4,5-tetrahydro-4-methyl-7,8-methylenedioxy-5-oxo-3-benzothiepin-2-carboxylic acid. (1R,2S)-norephedrine salt as colorless crystals [HPLC area percentage: (2R,4R):(2S,4S):(2S,4R):(2R,4S)= 0.7%:0%:3.7%:95.3%]

The norephedrine salt was further purified by repeating recrystallization from methanol to give colorless crystals [HPLC area percentage; (2R,4R):(2R,4S)=1.3%:98.1%], m.p.197.0–198.5 ° C.

Optical rotation $[\alpha]_D^{23}$ –195.5° C. (c 0.1, MeOH)

IR(cm$^{-1}$, KBr): 3290, 1663, 1630, 1400, 1258, 1075, 1050

$^1$H-NMR(CD$_3$OD, 300 MHz) δ 1.08(3H,d,J=6.8 Hz,Me), 1.42(3H,d,J=6.8 Hz, Me), 3.23(1H,dd,J=2.2,12.8 Hz), 3.36 (1H,dd,J=2.2,12.7 Hz), 3.43(1H,d,J=12.7 Hz), 3.47–3.51 (1H,m), 4.22(1H,q,J=7.0 Hz), 4.59(1H,br s), 4.93(1H,d,J= 3.5 Hz), 6.02(2H,s), 6.81(1H,s), 7.29–7.33(1H,m), 7.39(4H, m), 7.44(1H,s)

Elemental Analysis for C$_{22}$H$_{25}$NO$_6$S.H$_2$O:

Calcd.: C, 58.78; H, 6.05; N, 3.12

Found: C, 58.65; H, 6.00; N, 3.01.

WORKING EXAMPLE 2

Production of (2R,4S)-1,2,4,5-tetrahydro-4-methyl-7,8-methylenedioxy-5-oxo-3-benzothiepin-2-carboxylic Acid. (1S,2S)-2-amino-1-phenyl-1,3-propanediol Salt In 15 mL of THF was suspended 0.5 g of a racemic mixture, 1,2,4,5-tetrahydro-4-methyl-7,8-methylenedioxy-5-oxo-3-benzothiepin-2-carboxylic acid (content 99.5%; trans compound 88.1%, cis compound 11.4%). To the suspension was added 0.3 g (1 equivalent) of (1S,2S)-2-amino-1-phenyl-1,3-propanediol, which was made into a solution, followed by crystallization. The crystals were then aged for 30 minutes at room temperature (25° C.). The crystals were collected by filtration using, for example, glass filter, washed with 5 mL of THF, followed by drying overnight at room temperature under reduced pressure to afford 0.37 g of substantially pure (2R,4S)-1,2,4,5-tetrahydro-4-methyl-7,8-methylenedioxy-5-benzothiepin-2-carboxylic acid.(1S,2S)-2-amino-1-phenyl-1,3-propanediol salt as colorless crystals [HPLC area percentage; (2R,4R):(2S,4S):(2S,4R):(2R,4S)= 0.6%:0.6%:8.3%:85.6%].

WORKING EXAMPLE 3

Production of (2S,4R)-1,2,4,5-tetrahydro-4-methyl-7,8-methylenedioxy-5-oxo-3-benzothiepin-2-carboxylic Acid. (1S,2R)-norephedrine Salt In 340 mL of methanol was suspended 20.00 g of a racemic mixture, 1,2,4,5-tetrahydro-4-methyl-7,8-methylenedioxy-5-oxo-3-benzothiepin-2-carboxylic acid (content 100%; trans compound 87.1%, cis compound 12.9%). To the suspension was added 11.01 g (1 equivalent) of (1S,2R)-norephedrine at room temperature (25° C.), followed by stirring for 1 hour. The resulting crystals were collected by filtration, washed with 80 mL of cold methanol, and dried over one night at room temperature under reduced pressure to afford 10.39 g of substantially pure (2S,4R)-1, 2,4,5-tetrahydro-4-methyl-7,8-methylenedioxy-5-oxo-3-benzothiepin-2-carboxylic acid.(1S,2R)-norephedrine salt as colorless crystals [HPLC area percentage: (2R,4R):(2S, 4S):(2S,4R):(2R,4S)=0%:0.7%:94.2%:4.0%].

The norephedrine salt was further purified by repeating recrystallization from methanol to give colorless crystals (3.85 g) [HPLC area percentage: (2S,4S):(2S,4R)= 1.5%:97.9%].

WORKING EXAMPLE 4

Production of (2S,4R)-1,2,4,5-tetrahydro-4-methyl-7,8-methylenedioxy-5-oxo-3-benzothiepin-2-carboxylic Acid In 20 mL of water was dissolved 3.85 g of substantially pure (2S,4R)-1,2,4,5-tetrahydro-4-methyl-7,8-methylenedioxy-5-oxo-3-benzothiepin-2-carboxylic acid. (1S,2R)-norephedrine salt [HPLC area percentage: (2S,4S) :(2S,4R)=1.5%:97.9%]. To the solution was added 30 mL of 1N HCl, which was subjected to extraction by addition of 50 mL of THF and 50 mL of ethyl acetate. Organic layers were combined and washed twice with 30 mL each portion of water, dried over anhydrous MgSO$_4$, followed by concentration under reduced pressure to afford 2.42 g of substantially pure (2S,4R)-1,2,4,5-tetrahydro-4-methyl-7,8-methylenedioxy-5-oxo-3-benzothiepin-2-carboxylic acid as colorless crystals [HPLC area percentage: (2S,4S):(2S,4R)= 0.9%:98.9%].

WORKING EXAMPLE 5

Production of (2S,4R)-1,2,4,5-tetrahydro-4-methyl-7,8-methylenedioxy-5-oxo-3-benzothiepin-2-carboxylic Acid. (1R,2S)-norephedrine Salt In 12 mL of methanol was suspended 2.42 g of substantially pure (2S,4R)-1,2,4,5-tetrahydro-4-methyl-7,8-methylenedioxy-5-oxo-3-benzothiepin-2-carboxylic acid (content 99.8%; trans compound 98.9%, cis compound 0.9%). To the suspension was added 1.33 g (1 equivalent) of (1R,2S)-norephedrine.

Then, by substantially the same procedure as in Working Example 1, 1.47 g of substantially pure (2S,4R)-1,2,4,5-tetrahydro-4-methyl-7,8-methylenedioxy-5-oxo-3-benzothiepin-2-carboxylic acid.(1R,2S)-norephedrine salt was obtained as colorless crystals [HPLC area percentage; (2S,4S):(2S,4R)=0.4%:99.3%]. m.p.193.0–194.0° C.

Optical rotation $[\alpha]_D^{23}$+157.0° C. (c 0.1, MeOH)

IR(cm$^{-1}$, KBr): 3610, 1670, 1625, 1510, 1490, 1250, 1042

$^1$H-NMR(CD$_3$OD, 300 MHz) δ 1.08(3H,d,J=6.8 Hz,Me), 1.42(3H,d,J=6.8 Hz, Me), 3.23(1H,dd,J=1.9,12.7 Hz), 3.35 (1H,s), 3.37(1H,dd,J=2.0,13.0 Hz), 3.42(1H,d,J=12.6 Hz), 3.48–3.51(1H,m), 4.21(1H,q,J=7.0 Hz), 4.94(1H,d,J=3.5 Hz), 6.02(2H,s), 6.80(1H,s), 7.30–7.33(1H,m), 7.39(4H,m), 7.44(1H,s)

Elemental Analysis for C$_{22}$H$_{25}$NO$_6$S.0.5MeOH.0.5H$_2$O:

Calcd.: C, 59.19; H, 6.18; N, 3.07

Found: C, 58.95; H, 6.19; N, 2.94

WORKING EXAMPLE 6

Production of (2R,4S)-1,2,4,5-tetrahydro-4-methyl-7,8-methylenedioxy-5-oxo-3-benzothiepin-2-carboxylic Acid In 20 mL of 1N HCl was dissolved 2 g of substantially pure (2R,4S)-1,2,4,5-tetrahydro-4-methyl-7,8-methylenedioxy-5-oxo-3-benzothiepin-2-carboxylic acid. (1R,2S)-norephedrine salt [HPLC area percentage; (2R,4R) :(2S,4R)=0.5%:99.5%]. The solution was subjected to extraction twice with 20 mL each portion of ethyl acetate. The ethyl acetate layer was washed twice with 20 mL each portion of water, dried over anhydrous MgSO$_4$, followed by concentration under reduced pressure to afford 1.22 g of substantially pure (2R,4S)-1,2,4,5-tetrahydro-4-methyl-7,8-methylenedioxy-5-oxo-3-benzothiepin-2-carboxylic acid as colorless crystals [yield 94%, HPLC area percentage (2R,4R):(2R,4S)=0.6%:99.4%], m.p.194.0–195.0° C.

Optical rotation $[\alpha]_D^{23}$ –210.8° C. (c 0.50, MeOH)

IR(cm$^{-1}$, KBr): 1730, 1700, 1660, 1620, 1500, 1480, 1375, 1280, 1250, 1040

$^1$H-NMR(CDCl$_3$) δ 1.54(3H,d,J=7 Hz,Me), 3.22(1H,dd,J=5,15 Hz), 3.41(1H,dd,J=12,14 Hz), 3.60(1H,dd,J=5,12 Hz), 4.05(1H,q,J=7 Hz), 6.05(2H,q,J=1 Hz), 6.69(1H,s), 7.52 (1H,s)

Elemental Analysis for C$_{13}$H$_{12}$O$_5$S:

Calcd.: C, 55.71; H, 4.32

Found: C, 55.54; H, 4.38

WORKING EXAMPLE 7

Production of (2R,4S)-1,2,4,5-tetrahydro-4-methyl-7,8-methylenedioxy-5-oxo-3-benzothiepin-2-carboxylic Acid.(1R,2S)-norephedrine Salt In 500 mL of methanol-water (volume ratio 1:1) was suspended 50.6 g of a racemic mixture, 1,2,4,5-tetrahydro-4-methyl-7,8-methylenedioxy-5-oxo-3-benzothiepin-2-carboxylic acid (content 98.8%; trans compound 90.2%, cis compound 9.6%). To the suspension was added 25 mL of triethylamine, which was made into a solution by heating (50° C.). To the solution was added 13.6 g (0.5 equivalent) of (1R,2S)-norephedrine. The mixture was once made into a solution, which was crystallized in about 10 minutes, followed by cooling to 30° C. over about 60 minutes, and then to 5° C. The crystals were aged for 60 minutes at the same temperature. The resulting crystals were collected by filtration, washed with 200 mL of cold methanol-water (volume ratio 1:1) and dried at 35° C. under reduced pressure to afford 29.9 g of substantially pure (2R,4S)-1,2,4,5-tetrahydro-4-methyl-7,8-methylenedioxy-5-oxo-3-benzothiepin-2-carboxylic acid.(1R,2S)-norephedrine salt as colorless crystals [HPLC area percentage: (2R,4R):(2S,4S):(2S,4R):(2R,4S)=0.86%:0.46%:0.50%:97.9%].

WORKING EXAMPLE 8

Production of (2R,4S)-1,2,4,5-tetrahydro-4-methyl-7,8-methylenedioxy-5-oxo-3-benzothiepin-2-carboxylic acid.(1R,2S)-norephedrine salt To 1.33 L of methanol was added 300 g of a racemic mixture, 1,2,4,5-tetrahydro-4-methyl-7,8-methylenedioxy-5-oxo-3-benzothiepin-2-carboxylic acid (content 99.9%; trans compound 82.4%, cis compound 17.5%), followed by stirring for 5 minutes. The mixture was suspended by addition of 1.33 L of water. To the suspension was added 109.4 g of triethylamine, which was made into a solution by heating (50° C.). To the solution was added at a breath 81.6 g (0.5 equivalent) of (1R,2S)-norephedrine which was in advance dissolved with methanol-water (volume ratio 1:1). To the mixture thus obtained was added seed crystals of (2R,4S)-1,2,4,5-tetrahydro-4-methyl-7,8-methylenedioxy-5-oxo-3-benzothiepin-2-carboxylic acid.(1R,2S)-norephedrine salt, which was stirred for 12 minutes to result in crystallization. Crystallization and aging were carried out at 3 to 5° C. for 60 minutes after cooling to 32° C. over about 60 minutes and then cooling to 5° C. over about 60 minutes. The resulting crystals were collected by filtration, washed with 1000 mL of cold methanol-water (volume ratio 1:1), and dried at 35° C. under reduced pressure to afford 174.8 g of substantially pure (2R,4S)-1,2,4,5-tetrahydro-4-methyl-7,8-methylenedioxy-5-oxo-3-benzothiepin-2-carboxylic acid.(1R,2S)-norephedrine salt as colorless crystals (HPLC area percentage: (2R,4R):(2S,4S):(2S,4R):(2R,4S)=0.94%:0.31%:0.46%:98.0%].

WORKING EXAMPLE 9

Production of (2R,4S)-1,2,4,5-tetrahydro-4-methyl-7,8-methylenedioxy-5-oxo-3-benzothiepin-2-carboxylic Acid In 554 mL of acetone was suspended 138.4 g of substantially pure (2R,4S)-1,2,4,5-tetrahydro-4-methyl-7,8-methylenedioxy-5-oxo-3-benzothiepin-2-carboxylic acid.(1R,2S)-norephedrine salt [HPLC are percentage: (2R,4R):(2S,4S):(2S,4R):(2R,4S)=0.94%:0.31%:0.46%:98.0%]. To the solution was added 353 mL of 1N HCl to result in crystallization while dissolving. Crystallization and aging were conducted for 30 minutes at room temperature (28° C.), and crystallization and aging were conducted for further 30 minutes after addition of 478 mL of water. The resulting crystals were collected by filtration, washed with 830 mL of water and dried at 40° C. under reduced pressure to afford 81.4 g of substantially pure (2R,4S)-1,2,4,5-tetrahydro-4-methyl-7,8-methylenedioxy-5-oxo-3-benzothiepin-2-carboxylic acid as colorless crystals [yield 90.4%, HPLC area percentage: (2R,4R):(2S,4S):(2S,4R):(2R,4S)=0.09%:0%:0%:99.9%].

INDUSTRIAL APPLICABILITY

According to the method of this invention, an optically active benzothiepin derivative which is a raw material of an optically active compound useful as a prophylactic and therapeutic agent of bone diseases, namely (2R,4S)-1,2,4,5-tetrahydro-4-methyl-7,8-methylenedioxy-5-oxo-3-benzothiepin-2-carboxylic acid, can be efficiently produced by a simple and convenient procedure in a high purity with a good yield. The present invention thus provides a remarkably advantageous method on an industrial scale.

And, the optically active benzothiepin derivative which can be produced by the method of the present invention can be used as a material for synthesizing an optically active compound useful as a prophylactic and therapeutic agent of bone diseases which is described in EP-A-719782.

We claim:

1. A method of producing an amine salt of an optically active benzothiepin derivative, which is characterized by allowing a benzothiepin derivative represented by the formula:

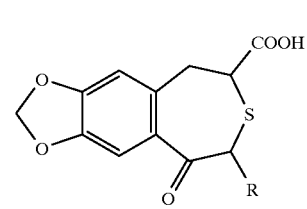

(I)

wherein R stands for a lower alkyl group, to react with an optically active amine, whereby the amine salt of the optically active benzothiepin derivative is obtained as an optically active form in a substantially pure state.

2. The method according to claim 1, in which R is methyl.

3. The method according to claim 1, in which the optically active amine is an optically active phenyl amino alkanol.

4. The method according to claim 3, in which the optically active phenyl amino alkanol is an optically active form of a compound represented by the formula:

$$R^1-CH-CH-CH_2R^5 \quad (II)$$
$$\phantom{R^1-CH}|\phantom{-CH-}|$$
$$\phantom{R^1-CH}OR^2\phantom{-}NR^3R^4$$

wherein $R^1$ stands for an optionally substituted phenyl group; $R^2$, $R^3$ and $R^4$ independently stand for H or a lower alkyl group; and $R^5$ stands for H, hydroxyl group, a lower alkyl group or a lower alkoxy group, or a salt thereof.

5. The method according to claim 4, in which the compound represented by the formula (II) is norephedrine.

6. A method of producing an optically active benzothiepin derivative, which is characterized by subjecting the amine salt of an optically active benzothiepin derivative as claimed in claim 1 to deamination.

7. An optically active form of a compound represented by the formula:

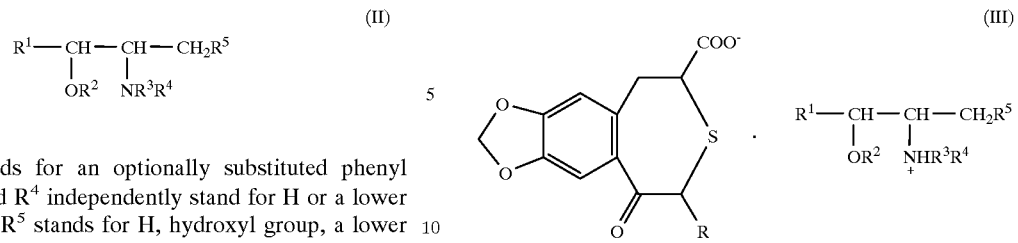

wherein R stands for a lower alkyl group; $R^1$ stands for an optionally substituted phenyl group; $R^2$, $R^3$ and $R^4$ independently stand for H or a lower alkyl group; and $R^5$ stands for H, hydroxyl group, a lower alkyl group or a lower alkoxy group.

8. The optically active form according to claim 7, which is (2R,4S)-1,2,4,5-tetrahydro-4-methyl-7,8-methylenedioxy-5-oxo-3-benzothiepin-2-carboxylic acid. (1R,2S)-norephedrine salt.

* * * * *

UNITED STATES PATENT AND TRADEMARK OFFICE
CERTIFICATE OF CORRECTION

PATENT NO.    : 5,952,512

DATED         : September 14, 1999

INVENTOR(S)   : YOSHIHARU MAEDA ET AL.

It is certified that error appears in the above-identified patent and that said Letters Patent is hereby corrected as shown below:

COLUMN 8

Line 66, "Acid." should read --acid.--; and
    Line 67, "Salt" should read --salt--.

COLUMN 9

Line 29, "$C_{22}H_{25}NO_6S.H_2O$:" should read --$C_{22}H_{25}NO_6S \cdot H_2O$:--'
    Line 35, "Acid." should read --acid·--;
    Line 36, "Salt" should read --salt--;
    Line 56, "Acid." should read --acid·--; and
    Line 57, "Salt" should read --salt--.

COLUMN 10

Line 12, "Acid" should read --acid--;
    Line 30, "Acid." should read --acid.--;
    Line 31, "Salt" should read --salt--;
    Line 40, "acid.(1R,2S)" should read --acid·(1R,2S)--; and
    Line 58, "Acid" should read --acid--.

UNITED STATES PATENT AND TRADEMARK OFFICE
CERTIFICATE OF CORRECTION

PATENT NO. : 5,952,512
DATED : September 14, 1999
INVENTOR(S) : YOSHIHARU MAEDA ET AL.

It is certified that error appears in the above-identified patent and that said Letters Patent is hereby corrected as shown below:

COLUMN 11

Line 17, "Acid." should read --acid·--;
    Line 18, "Salt" should read --salt--;
    Line 35, "acid.(1R,2S)" should read --acid·(1R,2S)--;
    Line 55, "acid.(1R,2S)" should read --acid·(1R,2S)--; and
    Line 65, "acid.(1R,2S)" should read --acid·(1R,2S)--.

COLUMN 12

Line 6, "acid." should read --acid·--;

COLUMN 14

Line 19, "acid." should read --acid·--.

Signed and Sealed this

Nineteenth Day of September, 2000

Attest:

Q. TODD DICKINSON

Attesting Officer      Director of Patents and Trademarks